United States Patent
Lentz et al.

(10) Patent No.: US 6,849,234 B2
(45) Date of Patent: *Feb. 1, 2005

(54) SYSTEM AND METHOD FOR CONTROLLING AN ULTRAVIOLET AIR TREATMENT DEVICE FOR RETURN AIR DUCT APPLICATIONS

(75) Inventors: Tracy L. Lentz, Minnetonka, MN (US); Timothy J. Kensok, Minnetonka, MN (US); Jeffrey M. Hammer, Maple Plain, MN (US); Mark E. Stout, Plymouth, MN (US); Richard N. Metzger, Pasadena, CA (US); Jon W. Orr, Thousand Oakes, CA (US)

(73) Assignee: Honeywell International Inc., Morristown, NJ (US)

( * ) Notice: Subject to any disclaimer, the term of this patent is extended or adjusted under 35 U.S.C. 154(b) by 453 days.

This patent is subject to a terminal disclaimer.

(21) Appl. No.: 09/995,068

(22) Filed: Nov. 26, 2001

(65) Prior Publication Data

US 2003/0099569 A1 May 29, 2003

(51) Int. Cl.$^7$ .............. A61L 2/00; G01D 11/26; B01J 19/08; F24F 3/16; G05D 23/00
(52) U.S. Cl. .............. 422/24; 422/1; 422/119; 422/121; 422/186.3; 422/305; 422/306; 422/900; 62/78; 62/264; 236/13; 236/16; 236/27; 236/49.3
(58) Field of Search .............. 422/1, 4–5, 22, 422/24, 119, 120–121, 186, 186.3, 305–307, 900, 906; 62/78, 264; 236/13, 16, 27, 49.3

(56) References Cited

U.S. PATENT DOCUMENTS

| | | | |
|---|---|---|---|
| 4,990,313 A | 2/1991 | Pacosz | 422/121 |
| 5,107,687 A | 4/1992 | Candeloro | 62/259.1 |
| 5,200,156 A | 4/1993 | Wedekamp | 422/186.3 |
| 5,225,167 A | 7/1993 | Wetzel | 422/121 |
| 5,558,274 A * | 9/1996 | Ben-Aissa et al. | 236/13 |
| 5,601,619 A | 2/1997 | Drechsler | 607/88 |
| 5,635,133 A | 6/1997 | Glazman | 422/24 |
| 5,742,063 A | 4/1998 | Scroggins et al. | 250/455.11 |
| 5,755,103 A | 5/1998 | Na et al. | 62/78 |
| 5,935,525 A | 8/1999 | Lincoln et al. | 422/121 |
| 5,968,455 A | 10/1999 | Brickley | 422/121 |
| 6,022,511 A | 2/2000 | Matschke | 422/121 |
| 6,063,170 A | 5/2000 | Deibert | 96/224 |
| 6,264,802 B1 | 7/2001 | Kamrukov et al. | 204/158.2 |
| 6,280,686 B1 | 8/2001 | Scheir et al. | 422/24 |
| 6,438,971 B1 * | 8/2002 | Lentz et al. | 62/78 |

OTHER PUBLICATIONS

A copy of the PCT Search Report, mailed Apr. 22, 2003 (6 pgs.).

Honeywell Brochure, "Comfort, Energy & Health Solutions," © Honeywell 2001.

Owner's Guide, "Enviracaire Elite—UV100E Ultraviolet Air Treatment System," 8 pgs, © Honeywell 2001.

* cited by examiner

*Primary Examiner*—Robert J. Warden, Sr.
*Assistant Examiner*—Monzer R. Chorbaji

(57) ABSTRACT

A system and method for controlling operation of an ultraviolet air treatment device including an ultraviolet lamp positioned to treat air within an air handling system that operates in either an on state or an off state. The method includes activating the ultraviolet lamp, and determining the operational state of the air handling system. The ultraviolet lamp is deactivated upon expiration of a predetermined time period during which the air handling system remains in the off state. The predetermined time period is preferably 30–60 minutes, preferably 40 minutes for residential applications.

23 Claims, 3 Drawing Sheets

SYSTEM AND METHOD FOR CONTROLLING AN ULTRAVIOLET AIR TREATMENT DEVICE FOR RETURN AIR DUCT APPLICATIONS

BACKGROUND OF THE INVENTION

The present invention relates to a system and method for controlling operation of ultraviolet lamps. More particularly, it relates to a system and method that optimizes lamp life of an ultraviolet air treatment device otherwise operating to reduce or eliminate microorganisms within an air handling system, especially in residential applications.

Though invisible to the naked eye, a multitude of airborne germs (e.g., bacteria, mold spores, etc.) exist, many of which have adverse implications for humans. The likelihood of inhaling or contacting one or more of these germs is elevated in enclosed areas, such as a home, office, etc. In most residential and commercial environments, an air handling system is in place, whereby outdoor air may be drawn into the home or building via a fresh air intake that merges with a return air duct, and then is subjected to heating or cooling conditions (e.g., via a furnace, air conditioner, etc.). As used throughout this specification, the phrase "air handling system" is in reference to a residential or commercial air handling system that has heating and/or cooling capabilities. The heated or cooled air is forced through auxiliary ductwork back to the rooms or offices. Thus, airborne germs entrained in the fresh and/or return airflow are effectively "concentrated" within the air handling system.

A commonly employed technique for eliminating airborne contaminants otherwise permeating through an air handling system is implementation of one or more air filters. While effective in removing a number of unwanted particles, these filters require relatively frequent replacement, and may not be able to consistently remove the smaller particle sized airborne germs. An alternative technique that has proven highly viable is the use of ultraviolet light/energy to kill airborne microorganisms.

In general terms, ultraviolet air treatment devices include one or more appropriately sized ultraviolet lamps that are positioned within the air handling system's ductwork. The ultraviolet lamp is normally mercury-based, with the ultraviolet air treatment device including a power supply ballast used to energize the mercury. For residential applications, the ultraviolet air treatment device is mounted to the outside of a return air duct of the air handling system, with the lamp(s) protruding inside of the duct itself. Alternatively, for other environmental applications, the ultraviolet air treatment device can be mounted to an appropriate duct (e.g., a re-circulation duct associated with a hospital clean room, etc.). Regardless, ultraviolet air treatment systems have proven highly effective in removing a vast majority of the airborne germs commonly encountered. One example of an ultraviolet air treatment device is available under the trade name "Enviracaire Elite UV100E Ultraviolet Air Treatment System" from Honeywell Inc., of Golden Valley, Minn.

Efforts have been made to improve the life and operational characteristics associated with ultraviolet air treatment lamps. For example, non-ozone producing lamps are now available. However, the method of controlling operation of the ultraviolet air treatment device has essentially remained unchanged. In particular, the ultraviolet lamp(s) is simply powered on following installation, and is never shut off. Regardless of whether the air handling system is active or inactive, the ultraviolet lamp(s) stays on twenty-four hours a day. While viable, this approach is quite inefficient in that when the air handling system is inactive, there is virtually no "new" air requiring ultraviolet energy treatment, so that powering of the ultraviolet lamp serves no purpose. As a result, continuous powering of the ultraviolet lamp needlessly consumes a relatively substantial portion of the lamp's useful life, thereby requiring more frequent lamp replacement (and thus increased maintenance costs) and excess energy consumption.

Alternatively, some existing ultraviolet air treatment systems control ultraviolet lamp activation/deactivation based directly upon operation of a fan otherwise associated with the air handling system. For example, most air heating systems including a fan or blower that draws air through the return duct and forces it past a furnace. These alternative control systems make use of the fact that airflows past the ultraviolet lamp only when the fan is operational to power the lamp on when the fan is on, and shut the lamp off when the fan is off. While this technique overcomes the performance issues of other control systems whereby the lamp inefficiently remains on during periods of air handling system inactivity, it does not serve to extend the lamp's useful life. In particular, the life cycle of low pressure mercury-based ultraviolet lamps is dictated not only by cumulative hours of lamp operation, but also by the number of lamp cycles (i.e., number of times the lamp is turned off and on). With this in mind, it has been found that deactivating/activating the ultraviolet lamp with every fan oscillation actually decreases the useful lamp life as the acceptable number of lamp cycles is quickly exceeded. Further, providing a direct electrical connection to the air handling system fan/blower (e.g., fan motor current monitor, sail switch, etc.) entails additional costs, low reliability, and installation complexities, giving rise to other potential limitations.

Ultraviolet air treatment devices continue to be highly popular for removal of airborne germs. In fact, ultraviolet air treatment devices are now becoming prevalent in residential applications. An obvious concern associated with these, and other installations, is cost. Unfortunately, currently available ultraviolet lamp control systems and methods overtly decrease a useful life of the ultraviolet lamp, either by inefficient lamp usage and/or unreasonable lamp cycling. Therefore, a need exists for a system and method for optimally controlling an ultraviolet air treatment device used, for example, to treat air within a return duct of an air handling system.

SUMMARY OF THE INVENTION

One aspect of the present invention relates to a method of controlling operation of an ultraviolet air treatment device including an ultraviolet lamp positioned to treat air within a duct of an air handling system. In this regard, the air handling system operates in either an on state or an off state. With this in mind, the method includes first activating the ultraviolet lamp. The operational state of the air handling system is then determined. Finally, the ultraviolet lamp is deactivated upon expiration of a predetermined time period during which the air handling system remains in the off state. In one preferred embodiment, the predetermined time period is in the range of 30–60 minutes, most preferably 40 minutes. In yet another preferred embodiment, the step of determining the operational state of the air handling system includes receiving information from an airflow sensor positioned within the duct. The airflow sensor is electrically connected to a control unit that controls activation of the ultraviolet lamp. Finally, the control unit is operated to monitor signals from the airflow sensor.

Another aspect of the present invention relates to a system for controlling operation of an ultraviolet air treatment device that includes an ultraviolet lamp positioned to treat air within a duct of an air handling system. In this regard, the air handling system operates in either an on state or an off state. With this in mind, the system includes an activation device and a controller. The activation device is electrically connected to, and adapted to control activation of, the ultraviolet lamp. The controller is electrically connected to the activation device. The controller is adapted to store predetermined time period value, as well as to prompt the activation device to activate the ultraviolet lamp. Further, the controller is adapted to receive information indicative of an operational state of the air handling system, as well as to determine whether the air handling system is in the off state or the on state based upon the received information. Finally, the controller is adapted to prompt the activation device to deactivate the ultraviolet lamp when the air handling system remains in the off state for an entirety of the predetermined time period. In one preferred embodiment, the system further includes a sensor electrically connected to the controller, with the sensor being adapted to signal information indicative of the operational state of the air handling system.

Yet another aspect of the present invention relates to an ultraviolet air treatment system for treating air within a duct of an air handling system. The ultraviolet air treatment system includes an ultraviolet lamp, an activation device, and a controller. The ultraviolet lamp is configured to be positionable within the air handling system duct. The activation device is electrically connected to the ultraviolet lamp and is able to dictate activation/deactivation of the ultraviolet lamp. Finally, the controller is electrically connected to the activation device for controlling operation thereof. In particular, the controller is adapted to store a predetermined time period value, and prompt the activation device to initiate activation of the ultraviolet lamp. Further, the controller is adapted to receive information indicative of an operational state of the air handling system, as well as to determine whether the air handling system is in an off state or an on state based upon the received information. Finally, the controller is adapted to prompt the activation device to subsequently deactivate the ultraviolet lamp upon determining that the air handling system has remained in the off state during an entirety of the predetermined time period. In one preferred embodiment, the controller is adapted to establish a lamp overrun sequence when first determining that the air handling system has switched from the on state to the off state, and then continually monitor the operational state of the air handling system for the predetermined time period. During this lamp overrun sequence, the controller maintains activation of the ultraviolet lamp.

DETAILED DESCRIPTION OF THE PREFERRED EMBODIMENTS

Figure 1:
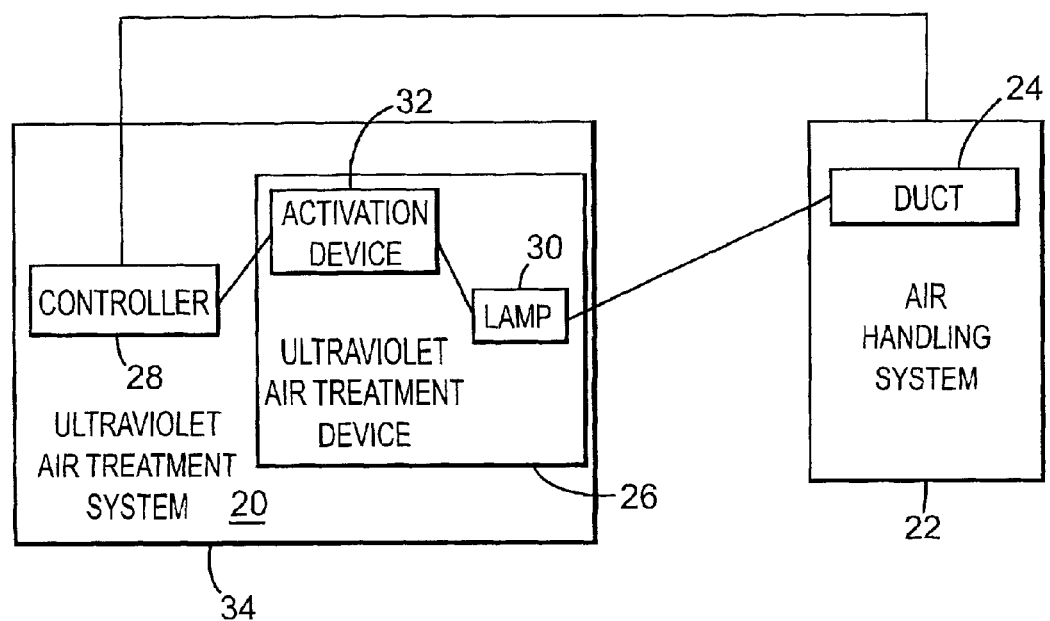
FIG. 1 is block diagram illustrating an ultraviolet air treatment system in conjunction with an air handling system.

One preferred embodiment of an ultraviolet air treatment system 20 is shown in block form in FIG. 1, in conjunction with an air handling system 22. As a point of reference, the air handling system 22 can assume a wide variety of forms appropriate for a particular residential, commercial or industrial application. Thus, the air handling system 22 can include a wide variety of air handling components (not shown), such as heating systems (e.g., furnace, heat pump, electric heat, etc.), cooling systems (e.g., air conditioner, swamp cooler, etc.), humidifiers, filters, etc. Further, the air handling system 22 can be constructed to direct heated, cooled and/or filtered air to a number of separate rooms, or can be installed to a single room. Regardless, the air handling system 22 operates in either an "off state" or an "on state", and includes a return air duct 24 through which air is cycled. In the off state, the air handling system 22 does not actively draw and/or force air through the return air duct 24. For example, where the air handling system 22 includes a blower/fan, when the fan/blower is off, the air handling system 22 is in the off state. Conversely, in the on state, the air handling system 22 is activated to force or draw air through the duct 24. For example, where the air handling system 22 includes a fan/blower, the on state is in reference to the fan/blower in an operation mode. In this regard, many fans associated with air handling systems 22 provide two or more speed settings (e.g. "high" and "low"); the air handling system in the on state so long as the fan is on, regardless of speed setting. Notably, reference to the particular "state" of the air handling system 22 is based solely upon whether the air handling system 22 is positively operating to draw or force air through the return air duct 24. Thus, it will be understood that in the off state, a negligible airflow or draft may occur through the return air duct 24.

With the above in mind, the ultraviolet air treatment system 20 includes an ultraviolet air treatment device 26 and a controller 28. The components are described in greater detail below. In general terms, however, the device 26 includes an ultraviolet lamp 30 and an activation device 32. The ultraviolet lamp 30 is positioned to protrude within the duct 24 of the air handling system 22. When activated by the activation device 32, the ultraviolet lamp 30 treats air within the duct 24 with ultraviolet energy. In this regard, the controller 28 is electrically connected to the activation device 32, and thus controls the ultraviolet lamp 30 based upon the operational state of the air handling system 22 as described in greater detail below.

Ultraviolet air treatment devices are well known in the art, such that the ultraviolet air treatment device 26 can assume a variety of forms. One acceptable ultraviolet air treatment device is available under the trade name "Enviracaire Elite, UV100E Ultraviolet Air Treatment System" from Honeywell Inc., of Golden Valley, Minn. In general terms, the ultraviolet air treatment device 26 includes a housing 34 (referenced generally in FIG. 1) that maintains the ultraviolet lamp 30 and the activation device 32. Further, the housing 34 is adapted for mounting to the duct 24. The ultraviolet lamp 30 can likewise assume a variety of forms, but is preferably a low pressure mercury lamp (e.g., mercury sealed within a protective structure). With this design, the activation device 32 preferably includes a ballast (magnetic or electronic) adapted to selectively power on and off the ultraviolet lamp 30. Alternatively, other devices able to directly turn the ultraviolet lamp 30 off and on are equally acceptable.

The controller 28 is electrically connected to the activation device 32 and is preferably a micro-processor based computer including associated memory and associated input/output circuitry. Alternatively, a programmable logic control (PLC) or other controller or equivalent circuitry can be employed. Further, while the controller 28 is illustrated as being contained within the housing 34, the controller 28 can be a separate component that is otherwise electrically connected to the activation device 32.

The controller 28 is adapted to prompt the activation device 32 to activate or deactivate the ultraviolet lamp 30 based upon certain constraints as described below. Further, the controller 28 is adapted to receive information from the air handling system 22 indicative of the operational state of the air handling system 22. For example, the controller 28 can be connected to an airflow sensor (not shown) positioned within the duct 24, connected to a fan/blower (not shown) associated with the air handling system 22, connected to another control device (e.g., thermostat, bussed universal environmental control unit, etc.) that otherwise relates to operation of the air handling system 22, etc. The controller 28 can be directly connected to any of these devices, or to a separate component that provides operational information for that device (e.g., a sail switch or current sensing relay electrically connected to the fan/blower). Regardless, the controller 28 is adapted to interpret the information provided by the air handling system 22 and determine the operational state thereof on a preferably continuous basis, as well as to evaluate the determined operational state during a lamp overrun sequence (described below) for purposes of determining whether lamp deactivation is appropriate. In this regard, the controller 28 stores a predetermined time period value that otherwise establishes a length of the lamp overrun sequence, as well as a clock or similar timing device.

Figure 2:
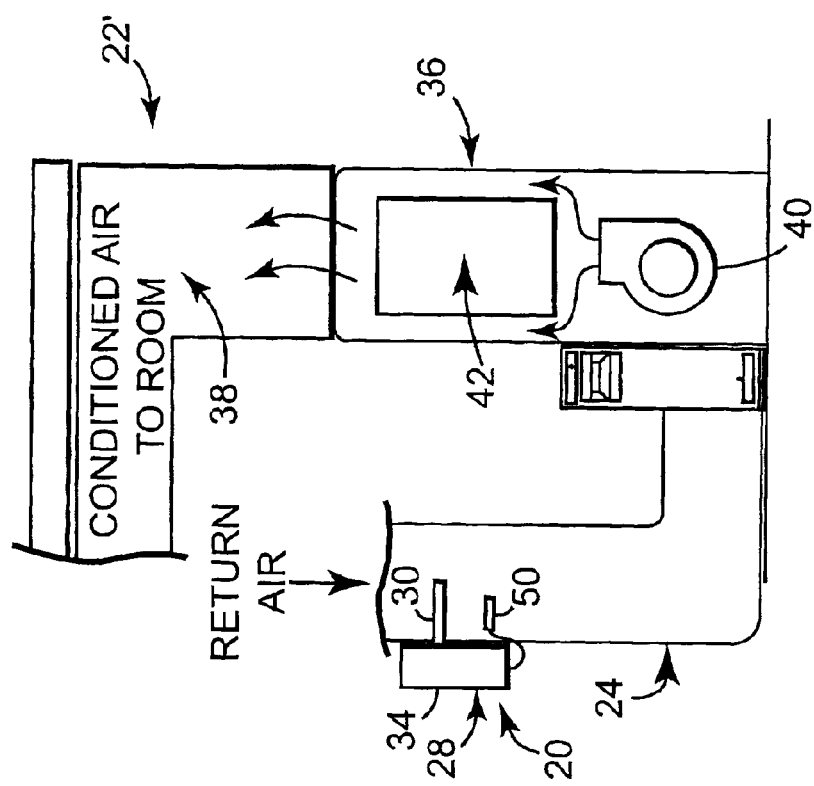
FIG. 2 is a diagrammatical illustration of the ultraviolet air treatment system of FIG. 1 as applied to a residential air handling system.

The above-described air treatment system 20 is illustrated in diagrammatical form in FIG. 2 in conjunction with one example of an air handling system 22'. With the one embodiment of FIG. 2, the air handling system 22' includes the return air duct 24, a furnace 36 and a supply duct 38. As previously described, the air handling system 22' can include additional components (e.g., filter, air conditioner, humidifier, etc.). In general terms, however, the air handling system 22' is installed within a structure (e.g., a home), with the return air duct 24 open to outdoor air. The furnace 36 is fluidly connected to the return air duct 24 and includes a fan/blower 40 and a heat exchanger 42. Upon activation, the fan/blower 40 operates to draw air into the air handling system 22' via the return air duct 24, and then into the furnace 36. Air heated by the heat exchanger 42 is then forced to the supply duct 38 that otherwise directs airflow to one or more rooms (not shown). With these designations in mind, the housing 34 of the ultraviolet air treatment system 20 is mounted to the return air duct 24 such that the ultraviolet lamp 30 extends within the duct 24. In this way, airflow directed through the return air duct 24 (such as by operation of the fan/blower 40) passes about the ultraviolet lamp 30, thereby effectuating destruction of airborne germs.

With the one preferred embodiment of FIG. 2, the ultraviolet air treatment system 20 further includes a sensor 50 that is secured within the return air duct 24, preferably near the ultraviolet lamp 30. The sensor 50 is electrically connected to the controller 28, and is adapted to generate a signal indicative of the operational state of the air handling system 22'. The sensor 50 is preferably an airflow sensor that detects the presence of more than nominal airflow through the duct 24. For example, the sensor 50 can include a heated temperature sensor (e.g., a thermistor) that is cooled by airflow through the duct 24, thereby indicating the presence of this airflow. Regardless, the controller 28 is capable of interpreting the airflow information generated by the sensor 50 as meaning that the air handling system 22' is in either the on state or the off state. Alternative airflow sensors (e.g., sail switch or current sensing relays), or any other type of sensor, are equally applicable.

Figure 3:
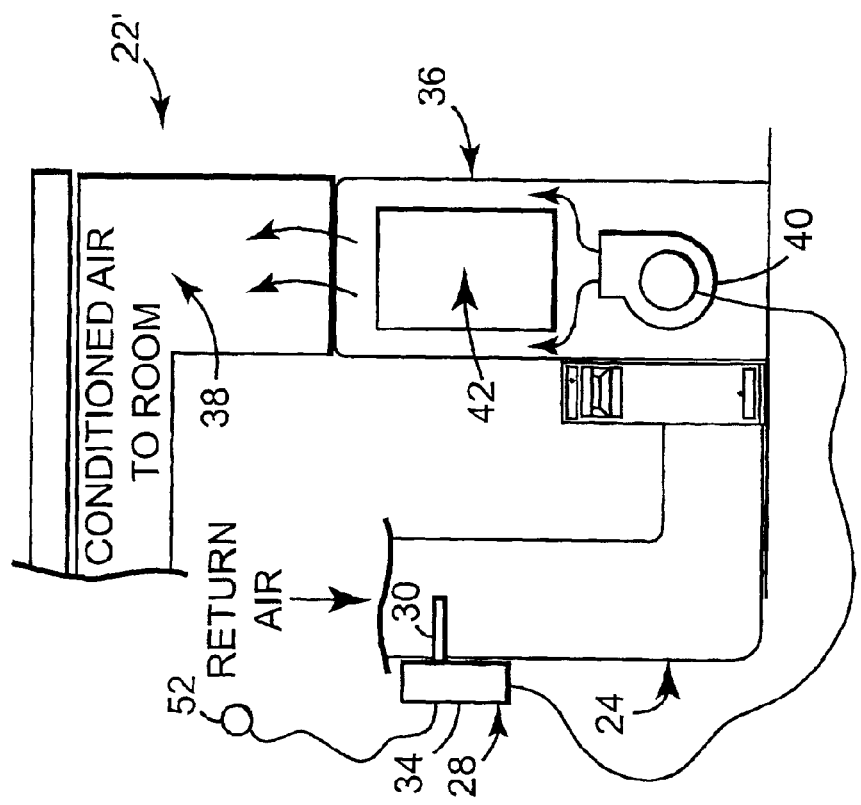
FIG. 3 is a diagrammatical illustration of an alternative application of the ultraviolet air treatment system of FIG. 1 as applied to a residential air handling system.

Alternative techniques for ascertaining the operational state of the air handling system 22' are provided by the diagrammatical view of FIG. 3. For example, the controller 28 can be connected to the fan/blower 40. With this connection, the controller 28 determines the operational state of the air handling system 22' based upon the operational state of the fan/blower 40. Alternatively, or in addition, the controller 28 can be electrically connected to an auxiliary component associated with the air handling system 22' such as a control unit 52. As is known in the art, the control unit 52 can be a thermostat that controls activation/deactivation of the air handling system 22', and thus can provide information indicative of the system's 22' operational state. Alternatively, the control unit 52 can be a computer-based, bussed universal control device that includes a communication bus from a thermostat, furnace fan board, etc. The universal control device 52 processes operational information from the thermostat or fan board relating to operation thereof, and delivers an appropriate signal to the controller 28 via the communications bus.

Figure 4:
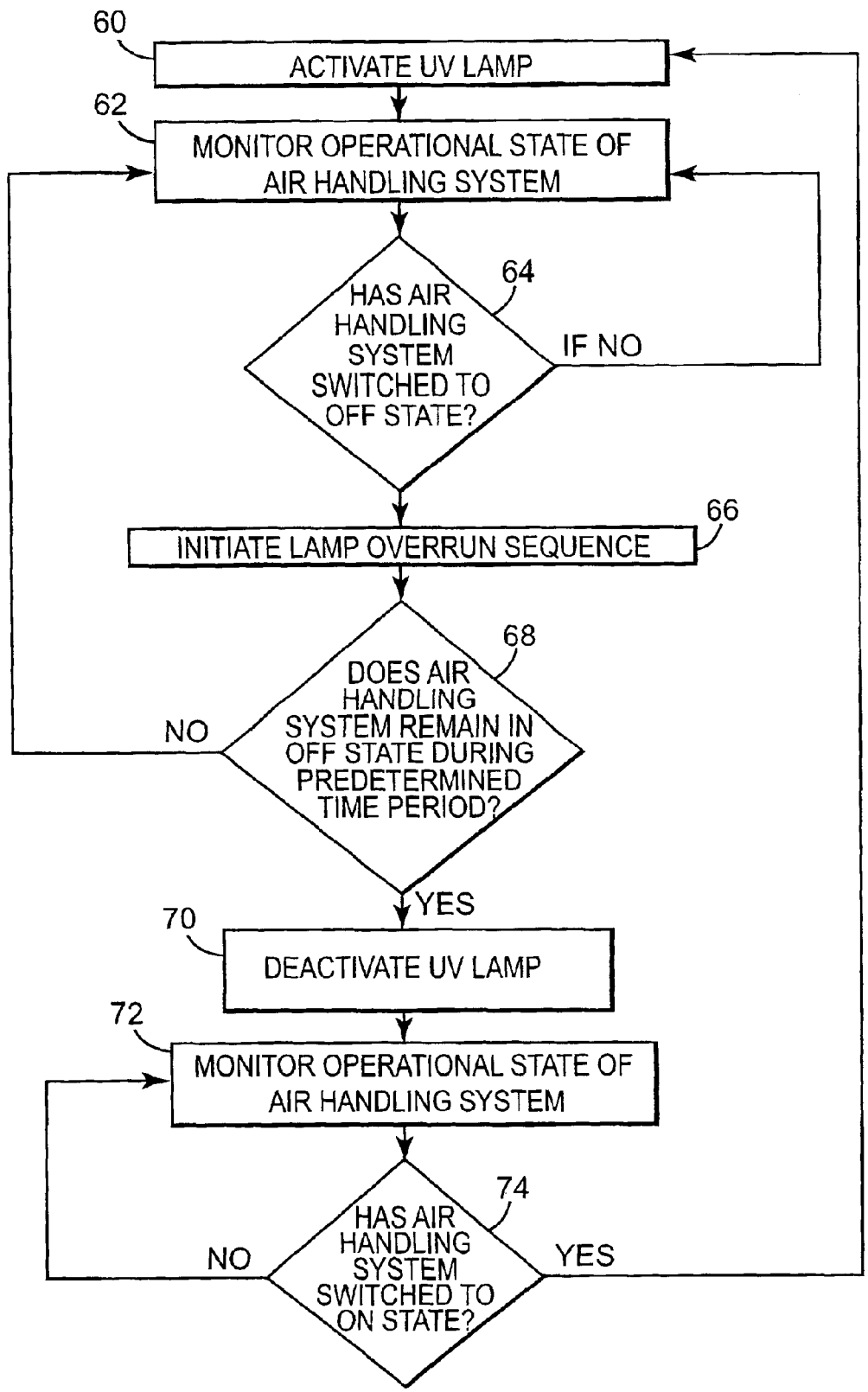
FIG. 4 is a flow diagram illustrating a method of controlling an ultraviolet air treatment device in accordance to the present invention.

Regardless of whether the ultraviolet air treatment system 20 incorporates a discrete sensor or is directly connected to a component of the air handling system 22', the preferred method of controlling operation of the ultraviolet air treatment device 26 is illustrated by the flow diagram of FIG. 4. Following installation to the air handling system 22, the controller 28 prompts the activation device 32 to activate the ultraviolet lamp 30 at step 60.

At step 62, the controller 28 monitors the operational state of the air handling system 22. As previously described, a wide variety of techniques are available for providing/signaling the controller 28 with information indicative of the operational state of the air handling system 22. For example, the airflow sensor 50, otherwise electrically connected to the controller 28, can be employed; a direct link to a fan/blower associated with the air handling system 22; a link to the thermostat 52; etc. Regardless, the controller 28 receives this information and, in conjunction with appropriate programming, interprets or determines the operational state. For example, where the ultraviolet air treatment system 20 incorporates the sensor 50 having at least one heated thermistor, the controller 28 interprets a relatively high temperature signal as indicating the air handling system 22 being in the off state, whereas a relatively low temperature reading is an indication of the air handling system 22 being in the on state.

As the controller 28 monitors the operational state of the air handling system 22, a determination is made as to whether the air handling system 22 has switched to the off state at step 64. If the air handling system 22 remains in the on state ("no" at step 64), the control method returns to step 62, and continues monitoring the operational state. Conversely, where a determination is made by the controller 28 that the air handling system 22 has switched to the off state ("yes" at step 64), the method proceeds to step 66 whereby a lamp overrun sequence is initiated.

The lamp overrun sequence entails maintaining activation of the ultraviolet lamp 30 over a predetermined time period during which the controller 28 continually confirms that the air handling system 22 remains in the off state. The predetermined time period is a value stored in a memory of the controller 28, and is preferably in the range of 30–60 minutes, preferably 40 minutes for residential applications.

Alternatively, other values can be employed. However, the preferred range, and even more preferred 40 minute value, has been found to dramatically improve the useful life of the ultraviolet lamp 30 as described in greater detail below.

With the above explanation of the lamp overrun sequence in mind, at step 68 the controller 28 continuously determines whether the air handling system 22 remains in the off state during an entirety of the predetermined time period. If, during the lamp overrun sequence, the air handling system 22 returns to the on state ("no" at step 68), the control method exits the lamp overrun sequence and returns to step 62. Conversely, where the air handling system 22 remains in the off state throughout the lamp overrun sequence ("yes" at step 68), the control method proceeds to step 70 whereby the controller 28 prompts the activation device 32 (FIG. 1) to deactivate the ultraviolet lamp 30.

With the ultraviolet lamp 30 deactivated, the controller 28 then monitors the operational state of the air handling system 22 as previously described at step 72. Based upon the determined operational state, the controller 28, at step 74, determines whether the air handling system 22 has switched to the on state. If the air handling system 22 remains in the off state ("no" at step 74), the monitoring function of step 72 is repeated. Conversely, where the controller 28 determines that the air handling system 22 has begun operating the on state ("yes" at step 74), the control method returns to step 60 whereby the controller 28 prompts re-activation of the ultraviolet lamp 30. The above-described control methodology is then repeated over the life of the ultraviolet lamp 30.

The system and method of the present invention overcomes the inefficiencies associated with the predominant technique of never turning the ultraviolet lamp 30 off following initial activation. In particular, the system and method of the present invention deactivates the ultraviolet lamp 30 when airflow is not present in the air handling system 22 for an extended period of time, thereby saving numerous hours of operation. Additionally, the system and method of the present invention obviates the excessive lamp cycling found with systems that activate/deactivate the ultraviolet lamp 30 each time the air handling system fan is oscillated. As a point of reference, a typical recommended lamp life associated with existing residential return air duct ultraviolet air treatment devices is approximately one year when the ultraviolet lamp is continuously powered on. The same device exhibits a useful lamp life of less than one year where ultraviolet lamp activation/deactivation is directly dictated by fan operation, due to excessive lamp cycling. In contrast, it has surprisingly been found that with the system and method of the present invention in which the above-described lamp overrun sequence employs a predetermined time period value of 40 minutes, the useful life of the ultraviolet lamp 30 generally increases to a minimum of two years. This dramatic improvement will be found in virtually every climate. In fact, simulations have been performed utilizing the above-described control methodology and highlighted an increase in lamp life from the manufacturer-recommended value of one year to approximately five years in a climate similar to that found in Tampa, Fla., approximately three years in a climate similar to that of Las Vegas, Nev., and approximately two years in a climate similar to that of Minneapolis, Minn.

In light of the above-described increase in useful lamp life, an additional feature preferably associated with the ultraviolet air treatment system 20 of the present invention is an ability to determine when the ultraviolet lamp 30 is approaching an end of its useful life, and providing an indication of this status to a user. In this regard, the controller 28 is preferably programmed to store a maximum run time value and/or a maximum cycle value (or some other lamp replacement-related maximum value). Further, the controller 28 records and accumulates actual running or activation time and total number of cycles for the ultraviolet lamp 30. When the actual, cumulative running time approaches the maximum run time value (e.g., within 10%) and/or the cumulative cycles approaches the maximum cycle value (e.g., within 10%), the controller 28 prompt a warning sequence in which an indication is given to a user that the ultraviolet lamp 30 should be replaced. For example, the controller 28 can prompt activation of a light, audible alarm, etc.

The system and method of the present invention provides a marked improvement over previous designs. The inefficiencies associated with constant powering of the ultraviolet lamp during periods in which the air handling system 22 is off are eliminated, while at the same time avoiding excessive lamp cycling.

Although the present invention has been described with reference to preferred embodiments, workers skilled in the art will recognize that changes can be made in form and detail without departing from the sprit and scope of the present invention.

What is claimed is:

1. A method of controlling operation of an ultraviolet air treatment device including an ultraviolet lamp positioned to treat air within a duct of an air handling system operational in an on state or an off state, the method comprising:
   a. activating the ultraviolet lamp;
   b. determining the operational state of the air handling system; and
   c. deactivating the ultraviolet lamp upon expiration of a predetermined time period during which the air handling system remains in the off state.

2. The method of claim 1, wherein the predetermined time period is in the range of 30–60 minutes.

3. The method of claim 2, wherein the predetermined time period is 40 minutes.

4. The method of claim 1, further comprising:
   initiating a lamp overrun sequence following step b, the lamp overrun sequence including continually monitoring the operational state of the air handling system during the predetermined time period, wherein the ultraviolet lamp remains activated during the lamp overrun sequence.

5. The method of claim 1, wherein determining the operational state includes receiving the information indicative of an operational state of the air handling system.

6. The method of claim 5, wherein receiving information indicative of an operational state includes:
   sensing the presence of airflow within the duct.

7. The method of claim 6, wherein sensing the presence of airflow includes:
   positioning a sensor within the duct, the sensor configured to provide a signal indicative of airflow;
   electrically connecting the sensor to a control unit otherwise controlling activation of the ultraviolet lamp; and
   monitoring signals from the sensor.

8. The method of claim 7, wherein the sensor includes a heated component adapted to be cooled when subjected to airflow.

9. The method of claim 5, wherein receiving information indicative of an operational state includes:
   monitoring a signal from a fan associated with the air handling system.

10. The method of claim 5, wherein receiving information indicative of an operational state includes:
monitoring a signal from a thermostat associated with the air handling system.

11. The method of claim 1, further comprising:
d. re-activating the ultraviolet lamp after step c upon determining that the air handling system has returned to the on state.

12. The method of claim 1, further comprising:
storing a lamp replacement value;
accumulating data during activation of the ultraviolet lamp, the data being related to the lamp replacement value; and
providing a warning signal when the accumulated data approaches the lamp replacement value.

13. A control system for controlling operation of an ultraviolet air treatment device including an ultraviolet lamp positioned to treat air within a duct of an air handling system operational in an on state or an off state, the control system comprising:
an activation device electrically connected to, and adapted to control activation of, the ultraviolet lamp; and
a controller electrically connected to the activation device and adapted to:
store a predetermined time period value,
prompt the activation device to activate the ultraviolet lamp,
receive information indicative of an operational state of the air handling system,
determine whether the air handling system is in the off state or the on state based upon the received information,
prompt the activation device to deactivate the ultraviolet lamp when the air handling system remains in the off state for an entirety of the predetermined time period.

14. The control system of claim 13, wherein the predetermined time period value is in the range of 30–60 minutes.

15. The control system of claim 14, wherein the predetermined time period value is 40 minutes.

16. The control system of claim 13, wherein the controller is further adapted to initiate a lamp overrun sequence upon determining that the air handling system has switched to the off state, the lamp overrun sequence including continually monitoring the operational state of the air handling system during the predetermined time period, and further wherein the controller is adapted to maintain activation of the ultraviolet lamp during the lamp overrun sequence.

17. The control system of claim 13, further comprising:
a sensor electrically connected to the controller, the sensor adapted to signal information indicative of the operational state of the air handling system.

18. The control system of claim 17, wherein the sensor is an airflow sensor positionable within the duct.

19. An ultraviolet air treatment system for treating air within a duct of an air handling system otherwise operational in an on state or an off state, the air treatment system comprising:
an ultraviolet lamp positionable within the duct;
an activation device electrically connected to the ultraviolet lamp for controlling activation of the ultraviolet lamp; and
a controller electrically connected to the activation device and adapted to:
store a predetermined time period value,
prompt the activation device to activate the ultraviolet lamp,
receive information indicative of an operational state of the air handling system,
determine whether the air handling system is in the off state or the on state based up on the received information,
prompt the activation device to deactivate the ultraviolet lamp when the air handling system remains in the off state for an entirety of the predetermined time.

20. The system of claim 19, wherein the predetermined time period value is in the range of 30–60 minutes.

21. The system of claim 20, wherein the predetermined time period value is 40 minutes.

22. The system of claim 19, further comprising:
a sensor electrically connected to the controller, the sensor adapted to signal information indicative of the operational state of the air handling system.

23. The system of claim 19, further comprising:
a control unit connected to the controller via a communication bus, the control unit adapted to signal information indicative of the operational state of the air handling system.

* * * * *